United States Patent [19]

Brewbaker et al.

[11] Patent Number: 5,071,942
[45] Date of Patent: Dec. 10, 1991

[54] MELT PROCESSABLE THERMOTROPIC AROMATIC COPOLYESTERS

[75] Inventors: James L. Brewbaker; William B. Marshall, both of Midland, Mich.

[73] Assignee: The Dow Chemical Company, Midland, Mich.

[21] Appl. No.: 581,449

[22] Filed: Sep. 10, 1990

Related U.S. Application Data

[63] Continuation of Ser. No. 354,065, May 19, 1989, abandoned.

[51] Int. Cl.[5] .................. C08G 63/00; C08G 63/02; C08G 63/18
[52] U.S. Cl. .................. 528/193; 528/176; 528/190; 528/194; 528/271; 528/272
[58] Field of Search .............. 528/176, 190, 193, 194, 528/271, 272

[56] References Cited

U.S. PATENT DOCUMENTS

| 4,333,907 | 6/1982 | Urasaki et al. | 528/193 |
| 4,447,593 | 5/1984 | Funakoshi et al. | 528/190 |
| 4,664,972 | 5/1987 | Connolly | 428/290 |
| 4,857,626 | 8/1989 | Kirshiro et al. | 528/176 |

Primary Examiner—John Kight, III
Assistant Examiner—T. Mosley

[57] ABSTRACT

The invention relates to a class of copolymers capable of forming an optically anisotropic melt comprising recurring structural units (a) independently each occurrence selected from the group consisting of Formula I; recurring structural units (b) independently each occurrence selected from the group consisting of Formulas II and III; recurring structural units (c) independently each occurrence selected from the group consisting of Formula IV and optionally recurring structural units (d) independently each occurrence selected from the group consisting of Formula V:

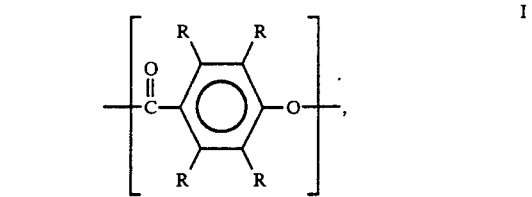

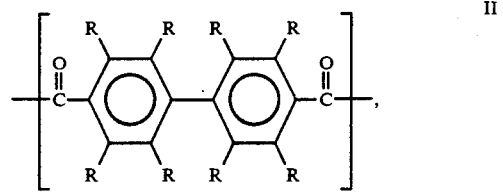

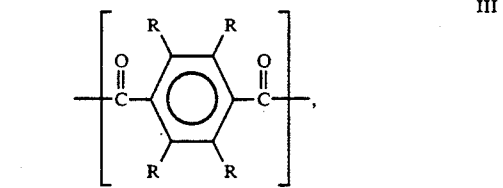

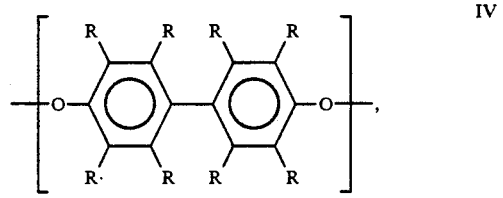

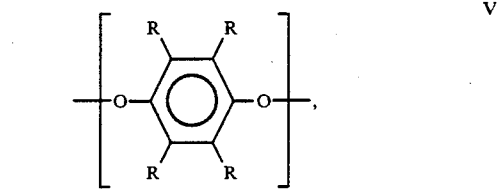

wherein R independently each occurrence is a chemically inert substituent.

10 Claims, No Drawings

MELT PROCESSABLE THERMOTROPIC AROMATIC COPOLYESTERS

CROSS-REFERENCE TO RELATED APPLICATION

This is a continuation of application Ser. No. 354,065, filed May 19, 1989, abandoned.

FIELD OF THE INVENTION

The invention relates to a class of copolyesters which display optical anisotropy in the molten state and to the shaped articles, fibers and films obtained from the optically anisotropic melts.

BACKGROUND OF THE INVENTION

Liquid crystalline polymers (LCPs) are macromolecules possessing significant orientation in either the molten state or in concentrated solution. The state of their solution (lyotropic) or melt (thermotropic) is between the boundaries of solid crystals and isotropic liquids. In the solid state these highly ordered polymers display exceptional strength properties in the direction of orientation. By designing molecules containing only relatively inert chemical bonds, preparation of thermally and oxidatively stable high-performance materials is possible.

A review of thermotropic LCPs can be found in Kwolek et al., "Liquid Crystalline Polymers", "*Encyclopedia of Polymer Science and Engineering*" 2nd Ed, Vol. 9, pp 23-55 (1987). Among those listed are polyesters. Many liquid crystalline polyesters display several of the desirable attributes of these compounds. Unfortunately, most have too high of a melt temperature for economical melt fabrication.

There is a growing need in the thermoplastic engineering industries to provide for new and improved polyesters and copolyesters which possess a high degree of processability while concurrently exhibiting superior mechanical properties.

SUMMARY OF THE INVENTION

The invention concerns copolymers capable of forming an optically anisotropic melt comprising recurring structural units (a) independently each occurrence selected from the group consisting of Formula I; recurring structural units (b) independently each occurrence selected from the group consisting of Formulas II and III; recurring structural units (c) independently each occurrence selected from the group consisting of Formula IV and optionally recurring structural units (d) independently each occurrence selected from the group consisting of Formula V:

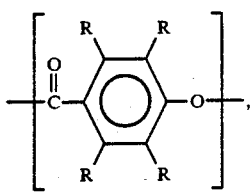

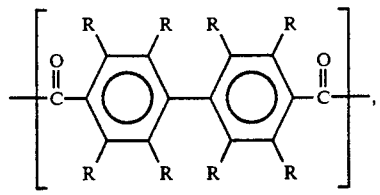

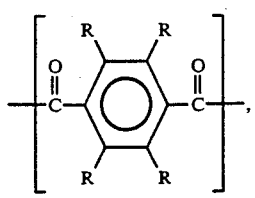

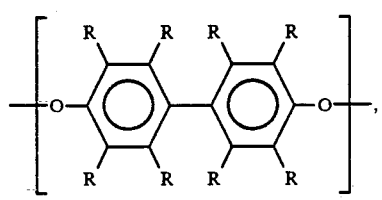

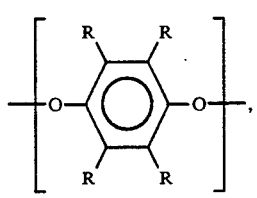

wherein R independently each occurrence is a chemically inert substituent.

DETAILED DESCRIPTION

Preferably, R is independently selected from the group consisting of hydrogen, halo, lower alkyl, methoxy and phenyl. Most preferably, R is each occurrence hydrogen.

In the copolyesters of the invention the molar percent ranges for independently recurring units of Formulas II and III substantially equal the molar percent ranges of the independently recurring units of Formulas IV and V.

Preferred molar percent ranges for these copolyesters are from 20 mole percent to 60 mole percent of independently recurring units of Formula I, from 20 mole percent to 40 mole percent of independently recurring units of Formulas II and III wherein the ratio of Formula II units to Formula III units varies from 20:80 to 80:20, and from 20 mole percent to 40 mole percent of independently recurring units of Formulas IV and V wherein the ratio of Formula IV units to Formula V units varies from 20:80 to 100:0.

More preferred molar percent ranges are from 40 mole percent to 60 mole percent of independently recurring units of Formula I, from 20 mole percent to 30 mole percent of independently recurring units of Formulas II and III wherein the ratio of Formula II units to Formula III units varies from 25:75 to 75:25, and from 20 mole percent to 30 mole percent of independently recurring units of Formulas IV and V wherein the ratio of Formula IV units to Formula V units varies from 25:75 to 75:25.

The most preferred molar percent ranges are from 45 mole percent to 55 mole percent of independently recurring units of Formula I, from 22.5 mole percent to 27.5 mole percent of independently recurring units of Formulas II and III wherein the ratio of Formula II units to Formula III units varies from 33:67 to 67:33, and from 22.5 mole percent to 27.5 mole percent of independently recurring units of Formulas IV and V wherein the ratio of Formula IV units to Formula V units varies from 33:67 to 67:33. The most preferred copolyesters of the invention melt below 350° C.

The copolymers may be formed by a variety of ester-forming techniques from difunctional organic compounds possessing functional groups which upon polycondensation form the requisite recurring units. For example, the functional groups of the organic aromatic compounds may independently contain carboxylic acid groups or acid halide groups and functional groups reactive therewith such as hydroxyl, or acyloxy groups. In a preferred embodiment, the organic reactants comprise lower acyloxy and carboxylic acid functionality. For example, lower acyl esters of 4,4'-dihydroxybiphenyl, 1,4-dihydroxybenzene and 4-hydroxybenzoic acid wherein the hydroxy group is esterified are more preferred as reactants. The lower acyl groups preferably have from 2 to 4 carbon atoms. Most preferably, the acetate esters are used.

The organic compounds may be allowed to react under anhydrous conditions in an inert atmosphere via a melt acidolysis procedure, in a suitable solvent via a solution procedure, or in a heat exchange medium via a slurry polymerization as described in Calundann, U.S. Pat. No. 4,067,852. Additional suitable reaction conditions are described in Schaefgen, U.S. Pat. No. 4,118,372. The teachings of the foregoing U.S. Patents are incorporated herein by reference. A preferable technique is the melt acidolysis technique.

A catalyst may or may not be used in the polymerization process. If one is used, representative catalysts for use in the process include dialkyl tin oxides (e.g., dibutyl tin oxide), diaryl tin oxides, titanium dioxide, alkoxy titanium silicates, titanium alkoxides, Lewis acids, hydrogen halides (e.g., HCl), alkali and alkaline earth metal salts of carboxylic acids (e.g., sodium acetate). The quantity of catalyst utilized typically is from 0.001 to 1 weight percent based upon total reactant weight, and most commonly from 0.01 to 0.2 weight percent. In a preferred method of polymerization, a catalyst is not used.

Liquid crystalline copolyester melts of this invention may be extruded into articles such as fibers which have outstanding strength and stiffness and will maintain their useful properties at elevated temperatures. Such fibers would be useful as tire cords, reinforcement in hoses, cables, conveyor belts or composite structures with matrixes prepared from other resinous materials. Articles may be films formed from the copolyesters which will have excellent solvent and chemical resistance. In addition, they should have low flammability and good electrical insulating properties. They would be useful as cable wrap, electric motor dielectric film and wire insulation. These copolyesters are useful for the manufacture of shaped articles such as those which are injection molded possessing high strength, stiffness, chemical resistance and low flammability.

Conventional additives and processing aids can be added to the copolyester melts of the invention to improve the properties of articles made therefrom. Examples of additives are oxidation stabilizers; heat stabilizers; ultraviolet light (UV) stabilizers; lubricants; mold release agents; dyes and pigments; fibrous or powdered fillers and reinforcing agents; nucleating agents; and plasticizers.

Examples of oxidation stabilizers and heat stabilizers are halides of metals of group I of the Periodic Table, used alone and used as a mixture with copper (I) halides or sterically hindered phenols in concentrations from 0.001 to 1 weight percent based on the weight of the copolyester composition.

Examples of UV stabilizers are substituted resorcinols, salicylates, benzotriazoles, benzophenones and mixtures of these, which are added, for example, in amounts from 0.001 to 2 weight percent based on the weight of the copolyester composition.

Dyes and pigments are used, for example, in amounts from 0.001 to 5 weight percent based on the weight of the copolyester composition. Examples are nigrosine, titanium dioxide, cadmium sulfide, phthalocyanine dyes, ultramarine blue and carbon black.

Examples of fillers and reinforcing agents are carbon fibers, glass fibers, amorphous silica, calcium silicate, aluminum silicate, magnesium carbonate, kaolin, chalk, powdered quartz, mica and feldspar, which may be present in a concentration from 0.5 to 70 weight percent, based on the total weight of the filled material.

Examples of nucleating agents are talc, calcium fluoride, sodium phenylphosphonate, alumina and finely divided polytetrafluoroethylene. Suitably, the nucleating agent may be present in an amount from 0.001 to 1 percent by weight.

Plasticizers, such as phthalates, hydrocarbon oils and sulfonamides can be included in an amount of from 0.0001 to 20 weight percent, based on the weight of the composition.

Also included in the composition of the invention, in addition to or in partial replacement of the reactants of Formulas I, II, III, IV, or V are amounts of other aromatic polymerizable units whose presence do not interfere with the excellent mechanical properties of these copolyesters. Examples of such aromatic units comprising these additional repeating units are isophthalic acid, resorcinol, 4,4'-isopropylidenediphenol, 3,4'-biphenyldicarboxylic acid and 3-hydroxybenzoic acid.

Preparation of 4-Acetoxybenzoic Acid

An amount of 4-hydroxybenzoic acid (92.1 grams (g), 0.67 mole) was dissolved in a solution of sodium hydroxide (NaOH) (53.4 g, 1.33 moles) and 1.33 liters (L) of water in a 4 L beaker. The solution was stirred and cooled to a temperature of 0° C. by adding crushed ice, then acetic anhydride (102.1 g, 1.00 mole) was added. The temperature was maintained at $-2°$ C. for 1 hour by adding one killogram (Kg) of crushed ice. A solution of concentrated hydrochloric acid (HCl) (144.7 g, 1.42 moles) in 267 milliliters (ml) of water was added. The slurry was stirred briefly and filtered. The product was washed twice by stirring it with 2 L portions of fresh water then filtered and dried in a vacuum oven at 80° C. for 16 hours. After recrystallization from methyl isobutyl ketone, the product consisted of 111 g of white crystals with a melting point (m.p.) of 192° C. to 192.5° C.

Preparation of 1,4-Diacetoxybenzene

The reaction was run in a 1-liter, single neck, round bottom flask equipped with a reflux condenser, nitrogen inlet, heating mantle and magnetic stirrer. Hydroquinone (88.0 g, 0.800 mole) and acetic anhydride (706 g, 6.9 moles) were added to the flask. The reaction mixture was heated to reflux at which time all of the hydroquinone had dissolved. The solution was refluxed for 18 hours, then the volatile fraction was removed to yield 191.2 g of crude 1,4-diacetoxybenzene. The crude product was recrystallized from 600 ml of methyl isobutyl ketone. The hot solution was filtered and allowed to cool overnight in a freezer. The clear, colorless crystals were isolated by filtration and dried in a vacuum oven at 75° C. for 4 hours. There remained 139.8 g of 1,4-diacetoxybenzene with a m.p. of 121.5° C. to 122.0° C.

Preparation of 4,4'-Diacetoxybiphenyl

An amount of 4,4'-biphenol (200 g, 1.07 moles), (Aldrich Chemical Company, Milwaukee, Wis.), and 1000 ml of acetic anhydride were added to a 2-liter boiling flask equipped with a cold water condenser and a polytetrafluoroethylene-coated magnetic stirring bar. The mixture was heated to reflux under nitrogen and all of the solid dissolved. The solution was refluxed for 20 hours, then cooled in a freezer at −15° C. overnight. The white crystals that were formed were isolated by filtration, washed with cold acetic anhydride and dried in a 100° C. vacuum oven overnight yielding 268.4 g of 4,4'-diacetoxybiphenyl with a m.p. of 162.7° C. to 164.0° C.

Preparation of 4,4'-Biphenyldicarboxylic acid

A 440 g portion of acetic acid, cobalt acetate tetrahydrate (1.25 g, 0.0033 mole), manganese acetate tetrahydrate (1.23 g, 0.0033 mole), potassium bromide (0.6 g, 0.005 mole), potassium acetate (1.48 g, 0.015 mole) and 4,4'-diisopropylbiphenyl (10 g, 0.042 mole) were added to a one-liter stirred titanium autoclave, which was then sealed. The reactor was then heated to 150° C., and 60 pounds per square inch (psi) of oxygen was introduced into the reactor to bring the total reactor pressure to about 150 psig. The reactor temperature was then raised to 180° C. and held for one hour. The reactor was then cooled to 50° C. and the carbon dioxide generated from oxidation was vented. The reactor was heated again to 180° C., then oxygen was introduced into the reactor which was kept at constant temperature for one hour. This procedure was repeated three more times. The reactor was cooled to room temperature and the contents filtered. A solid was obtained and washed with water and acetone to yield 9.4 g of a light brown solid, which was identical to 4,4'-biphenyldicarboxylic acid by infrared analysis.

Having described the invention, the following examples are provided as further illustrative and are not to be construed as limiting.

EXAMPLE I

Preparation of a Copolyester from 4-Acetoxybenzoic Acid, Terephthalic Acid, 1,4-Diacetoxybenzene, 4,4'-Biphenyldicarboxylic Acid and 4,4'-Diacetoxybiphenyl The polymerization was run in a 1 L, single neck, round bottom flask fitted with a two neck adapter upon which were mounted a paddle stirrer and a 13 centimeter (cm) Vigreaux distillation column, distillation head, condenser and receiver. An amount of 4-acetoxybenzoic acid (228.5 g, 1.268 moles), terephthalic acid (51.89 g, 0.3123 mole) Amoco* TA-33, (Amoco Chemical Company, Chicago, Ill.), 4,4'-biphenyldicarboxylic acid (75.66 g, 0.3123 mole), 1,4-diacetoxybenzene (60.65 g, 0.3123 mole) and 4,4'-diacetoxybiphenyl (84.42 g, 0.3123 mole) were added to the reaction flask. The apparatus was evacuated and refilled with nitrogen. The flask was immersed in a molten salt bath preheated to 285° C. When the solid reactants had melted, stirring was started and the temperature was slowly increased to 350° C. over a 100 minute period at atmospheric pressure. In the next 35 minutes the pressure was reduced to 2 mm Hg and maintained for 85 minutes. The vacuum was then released under nitrogen and the reaction vessel was removed from the 350° C. salt bath. The reaction apparatus was disassembled and the flask was broken away from the cooled, tan polymer plug. The plug was sawed into chunks and then ground in a Wiley mill. The copolyester comprised recurring units of Formulas I, II, III, IV and V wherein R is hydrogen.

The inherent viscosity of the copolyester prepared as described above was computed from the equation, $n_{inh} = (\ln n_{rel})/C$, where $\ln n_{rel}$ is the natural logarithm of the relative viscosity and C is the concentration in grams (g) of copolymer per deciliter (dl) of solution. Relative viscosity is the ratio of the polymer solution flow time to solvent flow time in a capillary viscometer at 45° C. The solvent used was pentafluorophenol. The concentration was 0.1 gram copolymer per deciliter of solution. The copolyester had an inherent viscosity of 8.4 dl/g.

Melt temperature analysis was carried out using differential scanning calorimetry (DSC) on a 15 mg compressed pellet at a heating and cooling rate of 20° C. per minute on a Mettler DSC-30 low temperature cell with a Mettler TC10A thermal analysis processor (Mettler Instrument Corp., Hightstown, N.J.). The copolyester showed peak melting points at 326° C. and 316° C. on the first and second heating scans of the DSC. On cooling, the copolyester showed a crystallization exotherm at approximately 285° C.

The copolyester was solid-state heat treated for 12 hours at 292° C. and at less than 0.1 mm Hg pressure to advance its molecular weight. The apparatus used for this treatment was a 1-liter round bottom flask connected to a rotating evaporator which was connected to a nitrogen/vacuum manifold. The apparatus was purged with nitrogen and evacuated. The flask was then lowered into a preheated salt bath and rotated for 12 hours. The melt viscosity of the copolyester at 330° C. and 352 seconds$^{-1}$ shear rate was increased from 211 poise to 1,650 poise after solid-state heat treatment.

The solid-state advanced copolyester was dried under vacuum for 14 hours at 100° C. and then injection molded into standard ⅛ inch tensile test bars using a Boy* 30-M Injection Molding Machine (Boy Machines Inc., Exton, Pa.). The barrel temperature was held at 330° C. the mold temperature at 88° C. and the injection pressure at 5 bars. Table I lists the tensile, flexural and impact properties of these bars measured using procedures described in ASTM Test No.'s D638, D790 and D256, respectively.

Optical anisotropy of the copolyester melts can be determined by examination of the materials with the use of an optical microscope. The equipment used for determining the optical anisotropy of the copolyesters of the present invention included a TH 600 hot stage, (Linkham Scientific Instruments LTD, Surrey, England) and a Nikon Optiphot Microscope equipped with crossed polarizers and a 35 mm camera (Nikon Instrument Group, Nikon, Inc., Garden City, N.Y.). A thin film of the polymer was optically anisotropic above its DSC-determined melting temperature when observed through a polarizing microscope.

TABLE I

| PROPERTY | VALUE |
| --- | --- |
| Tensile Strength | 17,600 psi |
| Tensile Modulus | 718,000 psi |
| Elongation | 5.38% |
| Flexural Strength | 14,800 psi |
| Flexural Modulus | 827,000 psi |
| Notched Izod Impact Strength | 9.14 ft lbs/inch |

EXAMPLE II

Preparation of a Copolyester from 1,4-Diacetoxybenzene, Terephthalic Acid, 4,4'-Diacetoxybiphenyl, 4,4'-Biphenyldicarboxylic Acid and 4-Acetoxybenzoic Acid Terephthalic acid (51.89 g, 0.3123 mole), Amoco* TA-33, (Amoco Chemical Company, Chicago, Ill.), 4-acetoxybenzoic acid (228.5 g, 1.268 moles), 1,4-diacetoxybenzene (61.40 g, 0.3162 mole), 4,4'-biphenyldicarboxylic acid (75.66 g, 0.3123 mole), and 4,4'-diacetoxybiphenyl (84.42 g, 0.3123 mole) were added to a reaction flask and polymerized using the procedure of Example I. The copolyester comprised recurring units of Formulas I, II, III, IV and V wherein R is hydrogen.

The inherent viscosity as determined using the methods of Example I was 9.2 dl/g. The peak melt temperatures as determined using the methods of Example I were 328° C. and 318° C. on the first and second heating scans, respectively. The copolyester gave a crystallization exotherm at approximately 285° C. on cooling.

The copolyester was injection molded using the methods of Example I. It was dried under vacuum. The mold temperature was 90° C., the barrel temperature was 335° C. and the injection pressure was eight bars. Table II shows the tensile, flexural and impact properties of the bars as determined by ASTM Test No.s D638, D790 and D256, respectively. The heat distortion temperature (HDT) was determined by thermomechanical analysis. A 9.9 mm in diameter pellet of the copolyester was compression molded and sanded to a 3.2 millimeter (mm) thick flat disk. A 9900 Thermal Mechanical Analyzer (DuPont Chemical Company, Wilmington, Del.) with a 0.635 mm diameter probe loaded with a 10 g weight was used for analysis of the sample. The temperature was increased at 5° C. per minute under nitrogen. The onset of the depression of the sample was taken as the HDT.

TABLE II

| PROPERTY | VALUE |
| --- | --- |
| Tensile Strength | 20,500 psi |
| Tensile Modulus | 1,110,000 psi |
| Elongation | 3.55% |
| Flexural Strength | 17,000 psi |
| Flexural Modulus | 1,370,000 psi |
| Notched Izod Impact Strength | 3.47 ft lbs/inch |
| HDT | 288° C. |

A thin film of the polymer was optically anisotropic above its DSC-determined melting temperature when observed through a polarizing microscope.

Example III

Copolyester of 4-Acetoxybenzoic Acid, Terephthalic acid, 4,4'-Biphenyldicarboxylic Acid, 4,4'-Diacetoxybiphenyl and 1,4-Diacetoxybenzene An amount of 4-acetoxybenzoic acid (19.16 g, 0.1063 mole), terephthalic acid (4.35 g, 0.0262 mole), 4,4'-biphenyldicarboxylic acid (6.348 g, 0.0262 mole), 4,4'-diacetoxybiphenyl (9.437 g, 0.0349 mole) and 1,4-diacetoxybenzene (3.390 g, 0.0175 mole) were melt polymerized according to the methods of Example I to give an opaque, tan-colored copolyester. The copolyester comprised recurring units of Formulas I, II, III, IV and V wherein R is hydrogen. The DSC analysis as used in Example I, showed a broad melting endotherm from 295° C. to 340° C. on the first heating scan, a crystallization exotherm at 290° C. on cooling and a peak melting temperature of 320° C. on the second heating scan.

A thin film of the polymer was optically anisotropic above its DSC-determined melting temperature when observed through a polarizing microscope.

Example IV

Copolyester of 4-Acetoxybenzoic Acid, Terephthalic Acid, 4,4'-Biphenyldicarboxylic Acid and 4,4'-Diacetoxybiphenyl An amount of 4-acetoxybenzoic acid (30.58 g, 0.1697 mole), terephthalic acid (6.944 g, 0.0418 mole), 4,4'-biphenyldicarboxylic acid (10.13 g, 0.0418 mole) and 4,4'-diacetoxybiphenyl (22.59 g, 0.0836 mole) were melt polymerized according to the methods of Example I to give an opaque, tan-colored copolyester. The copolyester comprised recurring units of Formulas I, II, III and IV wherein R is hydrogen. The DSC analysis as used in Example I, showed a peak melting temperature of 338° C. on the first heating scan, a crystallization exotherm at 295° C. on cooling and a broad melting endotherm from 300° C. to 350° C. on the second heating scan. A thin film of the polymer was optically anisotropic above its DSC-determined melting temperature when observed through a polarizing microscope using the methods of Example I.

Other copolyesters were prepared using the procedures of Examples I and II. The DSC-determined melting points (Tm) are shown in Table III. The table shows the mole fraction of each reactant wherein: 4-acetoxybenzoic acid (ABA), 4,4'-biphenyldicarboxylic acid (BPDCA), terephthalic acid (TA), 4,4'-diacetoxybiphenyl (DABP), 1,4-diacetoxybenzene (DAB) are the reactants.

TABLE III

| Mole Fraction of Each Reactant Added | | | | | Melting Temp |
| --- | --- | --- | --- | --- | --- |
| ABA | BPDCA | TA | DABP | DAB | Tm(°C.) |
| 0.504 | 0.124 | 0.124 | 0.000 | 0.248 | 358 |
| 0.504 | 0.124 | 0.124 | 0.038 | 0.210 | 349 |
| 0.504 | 0.124 | 0.124 | 0.075 | 0.173 | 331 |
| 0.504 | 0.124 | 0.124 | 0.124 | 0.124 | 320 |
| 0.504 | 0.124 | 0.124 | 0.165 | 0.083 | 320 |
| 0.504 | 0.124 | 0.124 | 0.248 | 0.000 | 338 |

What is claimed is:

1. A copolymer capable of forming an optically anisotropic melt consisting essentially of recurring structural units corresponding to the formulas:

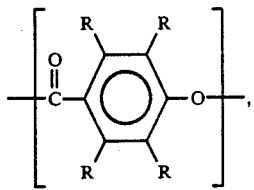

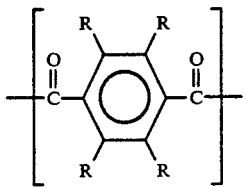

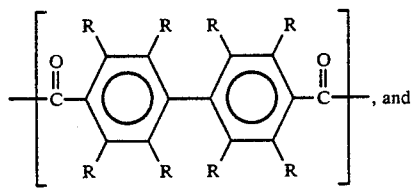, and

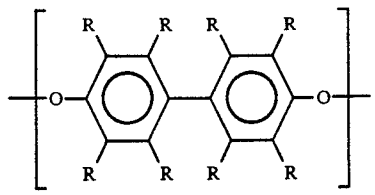

wherein each R is a chemically inert substituent.

2. The copolymer of claim 1 wherein R is independently selected from the group consisting of hydrogen, halo, lower alkyl, methoxy and phenyl.

3. An injection molded article of the copolymer of claim 1.

4. An oriented fiber of the copolymer of claim 1.

5. A film of the copolymer of claim 1.

6. A copolymer according to claim 1 additionally consisting essentially of recurring structural units corresponding to the formula:

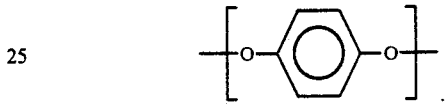

7. A copolymer of claim 6 wherein each R is selected from the group consisting of hydrogen, halo, lower alkyl, methoxy and phenyl.

8. An injection molded article of the copolymer of claim 6.

9. An oriented fiber of the copolymer of claim 6.

10. A film of the copolymer of claim 6.

* * * * *